United States Patent [19]

Tsubouchi et al.

[11] Patent Number: 4,609,481
[45] Date of Patent: * Sep. 2, 1986

[54] PROCESS FOR IMPROVING TRACTION COEFFICIENT OF TRACTION DRIVE FLUID AT HIGH TEMPERATURES

[75] Inventors: Toshiyuki Tsubouchi, Kisarazu; Hitoshi Hata, Ichihara, both of Japan

[73] Assignee: Idemitsu Kosan Company Limited, Tokyo, Japan

[*] Notice: The portion of the term of this patent subsequent to Jun. 25, 2002 has been disclaimed.

[21] Appl. No.: 736,549

[22] Filed: May 21, 1985

Related U.S. Application Data

[63] Continuation-in-part of Ser. No. 626,311, Jun. 29, 1984, Pat. No. 4,525,290, which is a continuation-in-part of Ser. No. 502,966, Jun. 10, 1983, abandoned.

[30] Foreign Application Priority Data

Jun. 24, 1982 [JP] Japan ............................. 57-107539
Feb. 21, 1983 [JP] Japan ............................. 58-26325

[51] Int. Cl.$^4$ ............................................. C07C 13/50
[52] U.S. Cl. ............................................ 252/73; 252/9; 585/20; 585/21; 585/360
[58] Field of Search ............... 252/9, 73; 585/20, 21, 585/360

[56] References Cited

U.S. PATENT DOCUMENTS 3,411,369 11/1968 Hammann et al. ............... 252/52 R
3,440,894 4/1969 Hammann et al. ............... 252/52 R
3,925,217 12/1975 Green et al. ..................... 252/52 R

FOREIGN PATENT DOCUMENTS 2081301 2/1982 United Kingdom .

Primary Examiner—Paul Lieberman
Assistant Examiner—Robert A. Wax
Attorney, Agent, or Firm—Walter H. Schneider

[57] ABSTRACT

A traction drive fluid composition comprising the principal component of at least one component represented by the general formula (I):

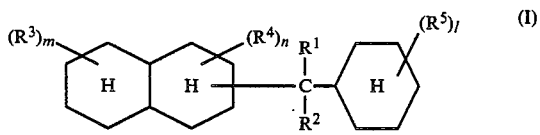

wherein $R^1$ to $R^5$ are each a hydrogen or an alkyl group containing from 1 to 4 carbon atoms, and 1, m and n are each 1 to 3, said compound (I) comprising a mixture of 70% or less of the cis-form and 30% or more of the trans-form.

18 Claims, 1 Drawing Figure

PROCESS FOR IMPROVING TRACTION COEFFICIENT OF TRACTION DRIVE FLUID AT HIGH TEMPERATURES

CROSS REFERENCE TO OTHER APPLICATION

This application is a continuation-in-part of application Ser. No. 626,311, filed June 29, 1984, now U.S. Pat. No. 4,525,290, which in turn is a continuation-in-part of application Ser. No. 502,966 filed June 10, 1983, now abandoned.

BACKGROUND OF THE INVENTION

The present invention relates to a process for improving traction coefficient of traction drive fluid at high temperatures. More particularly, it is concerned with a process for remarkably improving traction coefficient over a wide range of temperatures, especially at high temperatures by using specific compounds as a base stock of traction drive fluid.

A traction drive fluid is a fluid to be used in a traction drive (a friction driving device utilizing rolling contact), such as an automobile continuously variable transmission, an industrial continuously variable transmission, and a hydraulic machine, and needs to have a high traction coefficient and to be stable against heat and oxidation and be inexpensive.

In recent years, there has been the increasing trend toward miniaturization of a traction driving device using such a traction drive fluid and the use of such a device under high-speed, high-load conditions. Thus, it has been desired to develop a traction drive fluid of much higher performance.

In designing a traction driving device, it is generally said that the size of the traction driving device is in inverse proportion to the 0.45 power of a traction coefficient of a lubricant, provided that the traction driving device has the same service life and output ratio. Therefore, as the traction coefficient of a lubricant is higher, the traction driving device can be more reduced in size and weight. In this designing process, there is employed the minimum traction coefficient value in the temperature range within which the driving device is used; i.e., a traction coefficient value at the highest temperature within the foregoing temperature range because as the temperature increases, the traction coefficient value lowers. Therefore, a traction drive fluid having a high traction coefficient even at high temperatures is desirable for the miniaturization and weight-reduction of the traction driving device.

Also from a viewpoint of the use under high-speed, high-load conditions, it has been desired to develop a traction drive fluid having a high traction coefficient even at high temperatures.

Various types of compounds have been proposed as traction drive fluids. Examples are described in, e.g., U.S. Pat. Nos. 3,411,369, 3,440,894, 3,595,796, 3,595,797, 3,597,358, 3,598,740, 4,008,251, 3,645,902, 3,646,233, 3,975,208 and 4,329,529. Although these compounds all have a high traction coefficient at low temperatures (from room temperature to 80° C. (176° F.)), they have disadvantages in that at high temperatures (from 80° to 140° C. (176°-248° F.)) the traction coefficient drops, or although the traction coefficient does not drop, the viscosity is high, resulting in a serious stirring loss. This will lead to a reduction in power transmission efficiency.

Further, U.S. Pat. No. 3,411,369 discloses traction drive fluids comprising fused saturated hydrocarbons. Though the fluids have a high traction coefficient over a temperature range of from room temperature to 200° F., the traction coefficient of the fluids drops seriously at temperatures of more than 250° F. Therefore, these traction drive fluids cannot be used for continuously variable transmission for cars which is driven at high temperatures.

U.S. Pat. No. 3,440,894 discloses a compound having cyclic group as traction drive fluids, and U.S. Pat. No. 3,975,278 discloses hydrogenated compound of α-methylstyrene dimer as traction drive fluids. These compounds, however, have disadvantages in that the traction coefficient is lowered at high temperatures.

SUMMARY OF THE INVENTION

An object of the invention is to provide a process for improving traction coefficient at high temperatures.

Another object of the invention is to provide a process for reducing the change of traction coefficients over a wide range of from low temperature to high temperature.

Still another object of the invention is to provide a process for maintaining high traction coefficient even under severe conditions of high-speed and high-load, and over a long period of time.

The present invention relates to a process for improving traction coefficient of traction drive fluid at high temperatures by using a compound represented by the general formula (I) as a traction drive fluid;

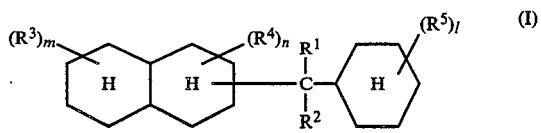

wherein $R^1$ to $R^5$ are each a hydrogen or an alkyl group containing from 1 to 4 carbon atoms, and l, m and n are each 1 to 3, said compound (I) comprising a mixture of 70% or less of the cis form and 30% or more of the trans form.

DETAILED DESCRIPTION OF THE INVENTION

Figure 1:
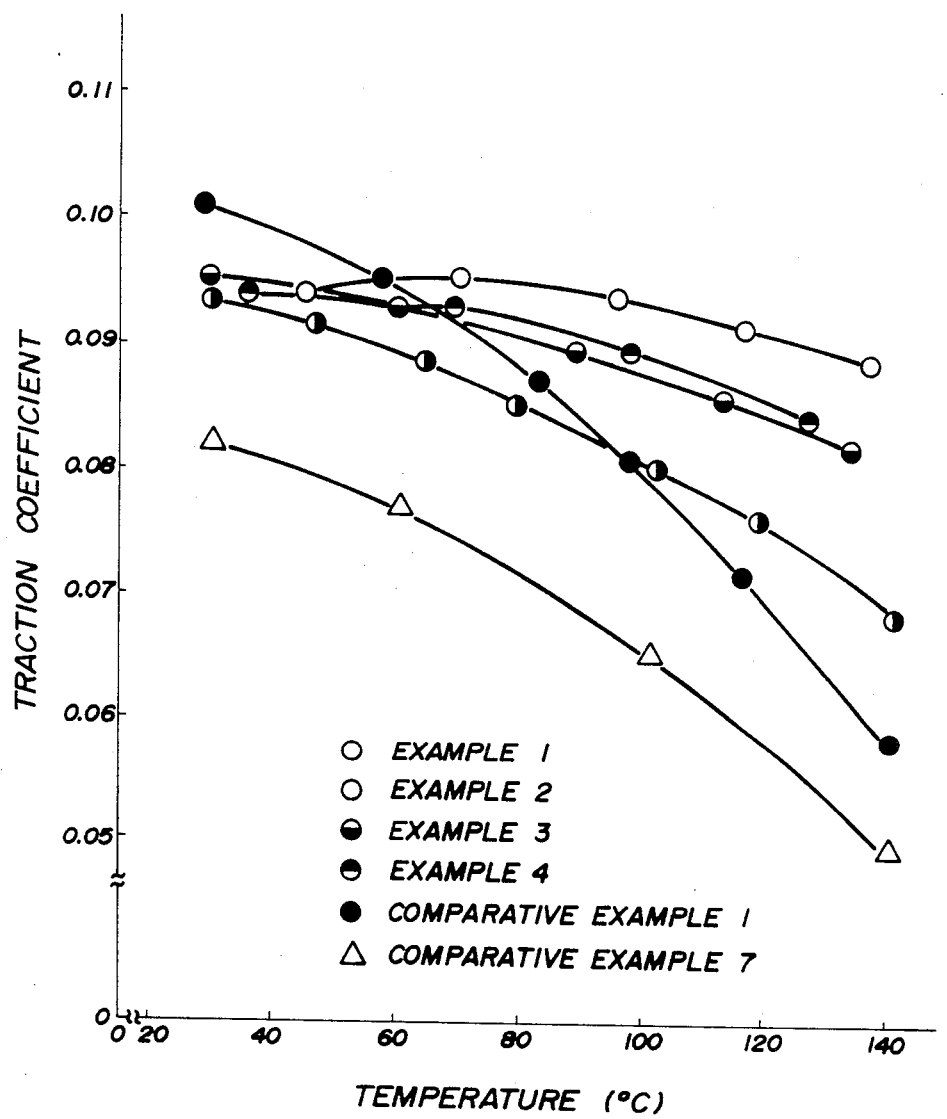
FIG. 1 is a graph showing the temperature dependence of traction coefficient for the products obtained in the Examples 1-4 and Comparative Examples 1 and 7.

The preferred components represented by the general formula (I) are represented by the general formula (II):

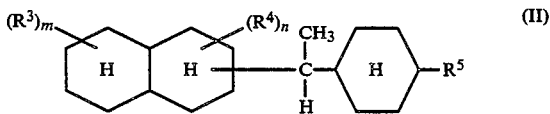

wherein $R^3$ and $R^4$ are each a hydrogen or a methyl group, $R^5$ is a hydrogen or a tert-butyl group, and m and n are each 1 or 2, Specific examples of the compounds represented by the general formula (I) are shown below:

1-(2-Decalyl)-1-cyclohexylethane (I-1)

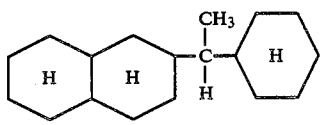

1-(1-Decalyl)-1-cyclohexylethane (I-2)

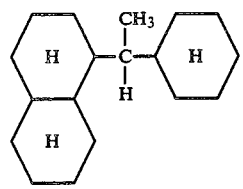

1-(2-Decalyl)-1-(4-(tert-butyl)cyclohexyl)ethane (I-3)

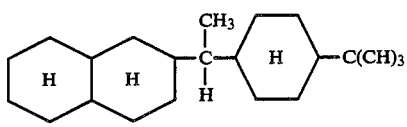

1-(1-Decalyl)-1-(4-(tert-butyl)cyclohexyl)ethane (I-4)

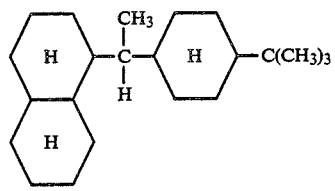

1-Dimethyldecalyl-1-cyclohexylethane (I-5)

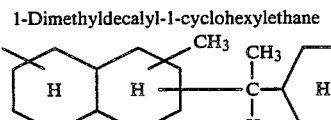

or

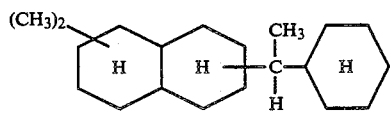

or

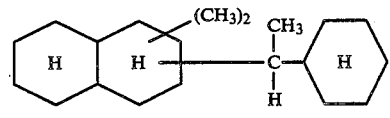

1-Methyldecalyl-1-cyclohexylethane (I-6)

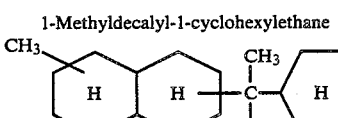

or

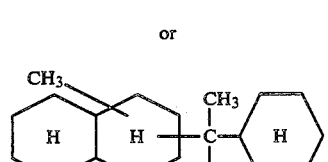

These compounds are used, alone or in combination with each other, as a base stock for a traction drive fluid.

The compounds represented by the general formula (I) can be prepared in any suitable manner.

As a typical method of preparation of the compounds of the general formula (I), there can be given a method in which tetralin or naphthalene, or its derivative, and styrene, or its derivative, is reacted in the presence of an acid catalyst, e.g., sulfuric acid, the thus-obtained reaction product is vacuum distilled into fractions, and a predetermined fraction is hydrogenated by the use of a catalyst.

In the present invention, a compound represented by the general formula I comprising a mixture of 70% or less of the cis-form and 30% or more of the trans-form is used. Preferably, the mixture comprises 30–60% of the cis-form and 70–40% of the trans-form.

The cis-form decalin ring herein means a decalin ring in which a hydrogen bonded to the carbon atom of 9-position and a hydrogen bonded to the carbon atom of 10-position are located in cis-position each other.

The thus-prepared compound having the general formula (I) can be used as such as a traction drive fluid, and it has a superior traction coefficient with less changes over a wide temperature range (from room temperature to 140° C. (284° F.) and has a low viscosity. Since the compounds represented by the general formula (I) can be prepared relatively inexpensively by the above-described methods, the traction drive fluids used in the invention are inexpensive and advantageous from an economic viewpoint.

Since the traction drive fluid used in the invention, as described above, has a superior traction coefficient over from low temperatures to high temperatures, it contributes to the miniaturization of driving devices. Furthermore, the present traction drive fluid can be used under severe conditions of high-speed and high-load.

In accordance with the process of the present invention, traction coefficient of traction drive fluids in the traction driving device which is driven at high temperatures of 200° F. (93.3° C.) to 250° F. (121.1° C.) or more is remarkably improved, and can be maintained at high level over a long period of time even under severe conditions. That is to say, traction drive fluids used in the present invention have higher traction coefficient at high temperatures than the conventional fluids, can be used efficiently over a long period of time, and are of high practical value. Therefore, the traction drive fluid of the invention can be widely used in various machines such as continuously variable transmission for cars or other industrial products and hydraulic machines.

The present invention is explained in greater detail by reference to the following Examples and Comparative Examples.

The traction coefficient was measured by the use of a two roller machine. One of two rollers, which were equal in size (diameter: 60 millimeters; thickness: 6 millimeters) and were in contact with each other along one line, was rotated at a predetermined rate (2,000 revolutions per minute (r.p.m.)), and the other was rotated at a predetermined lower rate (1,700 r.p.m.). A load of 140 kilograms was applied onto the contact line by means of a spring, and the torque was measured by means of a strain gauge and a torque meter. From the thus-measured value of torque, the traction coefficient was calculated. The two rollers were made of carbon steel, SCM-3, the surface of which was subjected to a buffing treatment using alumina (0.03 micron). The surface roughness was $R_{max}=0.2$ micron, and the Hertzian pressure in contact was 75 kilograms per square millimeter. This measurement was performed while changing the temperature of oil from room temperature to 120°–140° C. by heating an oil tank by means of a heater.

EXAMPLE 1

A mixture of 1,000 grams of tetralin and 300 grams of concentrated sulfuric acid was placed in a 3-liter glass flask, and the temperature in the flask was lowered to 0° C. on an ice bath. To the mixture was then slowly added dropwise 400 grams of styrene over 3 hours while stirring, and the resulting mixture was further stirred for 1 hour to complete the reaction. At the end of the time, stirring was stopped and the reaction mixture was allowed to stand to separate an oil layer. The oil layer was washed with 500 milliliters of a 1N aqueous solution of sodium hydroxide and 500 milliliters of saturated brine, three times for each, and then dried over anhydrous sodium sulfate. The unreacted tetralin was distilled away, and the residue was vacuum distilled to obtain 750 grams of a fraction having a boiling point of 135°–148° C./0.17 mmHg. Analysis showed that the fraction was a mixture of 1-(1-tetralyl)-1-phenylethane and 1-(2-tetralyl)-1-phenylethane.

Five hundred milliliters of the above-obtained fraction was placed in a 1-liter autoclave and, after addition of 50 grams of an activated nickel catalyst for hydrogenation (trade name: Catalyst N-113, produced by Nikki Kagaku Co., Ltd.), hydrogenated at a hydrogen pressure of 50 kilograms per square centimeter and a reaction temperature of 200° C. for 4 hours. After cooling, the reaction solution was filtered to separate the catalyst. Subsequently, a light fraction was separated from the resulting filtrate by stripping, and analyzed. This analysis showed that the degree of hydrogenation was over 99.9%, and it was confirmed that the light fraction was a mixture of 1-(1-decalyl)-1-cyclohexylethane and 1-(2-decalyl)-1-cyclohexylethane. The specific gravity of the mixture was 0.94 (15/4° C.), the dynamic viscosity was 4.2 centistokes (100° C.), and the refractive index, $n_D^{20}$, was 1.5025. The cis-form content was 42% in the mixture. The traction coefficient was measured over a temperature range of from 30° to 140° C. The results are shown in FIG. 1.

EXAMPLE 2

In the same manner as in Example 1 except that 550 grams of p-(tert-butyl)styrene was used in place of styrene, 800 grams of a fraction having a boiling point of 180°–190° C./0.9 mmHg was obtained. Analysis showed that the fraction was a mixture of 1-(1-tetralyl)-1-(p-(tert-butyl)phenyl)ethane and 1-(2-tetralyl)-1-(p-(tert-butyl)phenyl)ethane.

The fraction was then subjected to a hydrogenation treatment and stripping in the same manner as in Example 1. The thus-obtained product was a mixture of 1-(1-decalyl)-1-(4-(tert-butyl)cyclohexyl)ethane and 1-(2-decalyl)-1-(4-(tert-butyl)cyclohexyl)ethane. The specific gravity of the mixture was 0.92 (15/4° C.), the dynamic viscosity was 10 centistokes (100° C.), and the refractive index, $n_D^{20}$, was 1.4998. The cis-form content was 45% in the mixture. The traction coefficient of the product was measured over a temperature range of from 40° to 140° C. The results are shown in FIG. 1.

EXAMPLE 3

In accordance with the same process as in Example 1 except that 1,000 grams of dimethylnaphthalene (a dimethylnaphthalene mixture produced by Wako Junyaku Co., Ltd.) was used in place of tetralin, a mixture of 1-(1-dimethyl-decalyl)-1-cyclohexylethane and 1-(2-dimethyldecalyl)-1-cyclohexylethane was produced. The specific gravity of the mixture was 0.93 (15/4° C.), the dynamic viscosity was 5.6 centistokes (100° C.), and the refractive index, $n_D^{20}$, was 1.5007. The cis-form content was 40% in the mixture. The traction coefficient of the product was measured over a temperature range of from 40 to 140° C. The results are shown in FIG. 1.

EXAMPLE 4

In accordance with the same process as in Example 1 except that a mixture of 500 grams of α-methylnaphthalene and 500 grams of β-methylnaphthalene was used in place of tetralin, a mixture of 1-(1-methyldecalyl)-1-cyclohexylethane and 1-(2-methyldecalyl)-1-cyclohexylethane was produced. The specific gravity of the mixture was 0.94 (15/4° C.), the dynamic viscosity was 5.8 centistokes (100° C.), and the refractive index, $n_D^{20}$, was 1.5069. The cis-form content was 42% in the mixture. The traction coefficient of the product was measured over a temperature range of from 40° to 130° C. The results are shown in FIG. 1.

COMPARATIVE EXAMPLE 1

A mixture of 1,000 grams of α-methylstyrene, 50 grams of acidic terra abla, and 50 grams of ethylene glycol was placed in a 3-liter glass flask, and reacted with stirring at 140° C. for 2 hours. The catalyst was removed from the reaction solution by filteration. Then, the unreacted α-methylstyrene and ethylene glycol were distilled away to obtain 900 grams of a fraction having a boiling point of 125°–130° C./0.2 mmHg. NMR analysis and gas chromatographic analysis confirmed that the fraction was a mixture consisting of 95% α-methylstyrene linear dimer and 5% α-methylstyrene cyclic dimer.

Five hundred milliliters of the fraction was placed in a 1-liter autoclave and, after addition of 50 grams of an activated nickel catalyst for hydrogenation (Catalyst N-113 produced by Nikki Kagaku Co., Ltd.), hydrogenated at a hydrogen pressure of 50 kilograms per square centimeter and a reaction temperature of 200° C. After cooling, the reaction solution was filtered to separate the catalyst. The resulting solution was subjected to stripping of the light fraction to obtain a traction drive fluid composed mainly of 2,4-dicyclohexyl-2-methylpentane. The refractive index, $n_D^{20}$, of the thus-formed fluid was 1.4902, the specific gravity was 0.90 (15/4° C.), the dynamic viscosity was 3.7 centistokes (100° C.), and the viscosity index was 16. The traction coefficient was measured over a temperature range of from 30° C. to 140° C. The results are shown in FIG. 1.

EXAMPLE 5

Traction drive test of Cone-Roller toroidal type continuously variable transmission as disclosed in "The American Society of Mechanical Engineers" 83/WA/DSC-33, was carried out using, as the traction drive fluid, 1-decalyl-1-cyclohexylethane (cis-form content: 42%) prepared in accordance with Example 1 and 0.5 wt % of zinc dialkyldithiophosphate (ZnDTP) as additive.

The test conditions were as follows.
Input Disk Speed: 3000 r.p.m.
Input Torque: 3.0 kg·f·m Speed Ratio: 1:1
Oil Temperature: 25°-130° C.
The test was started at an oil temperature of 25° C., and the oil was gradually heated up to 130° C. by the electric heater. Input torque was transmitted at 130° C. without any trouble.

COMPARATIVE EXAMPLE 2

The procedure of Example 5 was repeated except that 2,4-dicyclohexyl-2-methylpentane prepared in accordance with Comparative Example 1 was used in place of 1-decalyl-1-cyclohexylethane.

Input torque could not be transmitted at oil temperatures of 114° C. or more since the transmission was slipped.

COMPARATIVE EXAMPLE 3

The procedure of Example 5 was repeated except that the traction drive fluid was replaced by a traction drive fluid commercially available from Monsanto Company under the trademark Santotrac 50.

Input torque could not be transmitted at oil temperatures of 105° C. or more since the transmission was slipped.

EXAMPLE 6 and COMPARATIVE EXAMPLE 4

Oxidation stability tests were conducted on the traction drive fluids of Example 5 and Comparative Example 3 in accordance with ASTM D 2272-67. The results are shown in Table I. As seen from Table I, 1-decalyl-1-cyclohexylethane has a superior oxidation stability.

TABLE I

| No. | Fluid Composition | | Induction Period (Min.) |
|---|---|---|---|
| | Base Oil | Additives (Pts/wt) | |
| EXAMPLE 6 | 1-Decalyl-1-cyclohexyl-ethane | ZnDTP 0.05* | 300 |
| COMPARATIVE EXAMPLE 4 | Santotrac 50 | — | 125 |

*Calculated as metallic zinc

EXAMPLE 7 and COMPARATIVE EXAMPLE 5

Oxidation stability data were conducted on the traction drive fluids of Example 5 and Comparative Example 3 in accordance with JIS K 2514. The results are shown in Table II. As seen from Table I, 1-decalyl-1-cyclohexylethane has a superior oxidation stability and a superior metal corrosion resistance.

EXAMPLE 8 and COMPARATIVE EXAMPLE 6

Tests for Extreme-Pressure properties of lubricating fluids were conducted on the traction drive fluids of Example 5 and Comparative Example 3 in accordance with ASTM D 2783-82. The results are shown in Table III. As seen from Table III, 1-decalyl-1-cyclohexylethane has a superior load carrying capacity.

TABLE III

| No. | Fluid Composition | | Corrected load (kgf) | Load-Wear Index (kgf) | Weld Point (kgf) |
|---|---|---|---|---|---|
| | Base Oil | Additives (Pts/wt) | | | |
| EXAMPLE 8 | 1-Decalyl-1-cyclohexyl-ethane | ZnDTP 0.05* | 75.2 | 33.5 | 160 |
| COMPARATIVE EXAMPLE 6 | Santotrac 50 | — | 48.8 | 28.8 | 250 |

*Calculated as metallic zinc

COMPARATIVE EXAMPLE 7

A mixture of 1,452 grams (11.0 moles) of tetralin, 23.0 grams (1.0 mole) of metallic sodium and 6.67 grams (0.11 mole) of isopropyl alcohol was placed in a 5-liter glass flask under an atmosphere of argon gas, and the temperature in the flask rose to 135° C. While vigorously stirring the mixture, 416 grams (4.0 moles) of purified styrene and 132 grams (1.0 mole) of tetralin were slowly dropped to the mixture over 3 hours at temperatures of 135° to 140° C. Thereafter, the resulting mixture was further stirred for 1 hour to complete the reaction. After that, the reaction product was cooled to room temperature. Methanol was slowly dropped to the product under stirring to decompose metallic sodium unreacted. After introduction of argon gas was stopped, the product in the flask was transferred into a separatory funnel to wash with water. An oil layer obtained by removing an aqueous layer from the product was distilled in vacuum to obtain 302 grams (1.28 moles) of 1-(1-(1,2,3,4-tetrahydronaphthyl))-2-phenyl ethane, the yield of which was 32 mole % based on styrene.

Three hundred milliliters of the above-obtained fraction was placed in a 1-liter autoclave and, after addition of 30 grams of an activated nickel catalyst for hydrogenation (trade name: Catalyst N-113, produced by Nikki Kagaku Co., Ltd.), hydrogenated at a hydrogen pressure of 50 kilograms per square centimeter and a reaction temperature of 200° C. for 4 hours. After cooling, the reaction solution was filtered to separate the catalyst. Subsequently, a light fraction was separated from the resulting filtrate by stripping, and analyzed. This analysis showed that the degree of hydrogenation 99.9% and the obtained compound was 1-(1-decalyl)-2-cyclohexylethane. The specific gravity of the mixture was 0.93 (15/4° C., the dynamic viscosity was 4.2 centi-

TABLE II

| No. | Fluid Composition | | | Viscosity (cSt) | | Total Acid Value (mgKOH/g) | Sludge | Appearance of Catalyst | |
|---|---|---|---|---|---|---|---|---|---|
| | Base Oil | Additives (Pts/wt) | | 40° C. | 100° C. | | | Cu | Fe |
| EXAMPLE 7 | 1-Decalyl-1-cyclohexyl-ethane | ZnDTP 0.05* | Before Test | 42.15 | 6.283 | 0.78 | — | — | — |
| | | | After Test | 47.51 | 6.590 | 0.88 | None | No Change | No Change |
| COMPARATIVE EXAMPLE 5 | Santotrac 50 | — | Before Test | 31.18 | 5.698 | 1.32 | — | — | — |
| | | | After Test | 41.98 | 7.279 | 1.68 | Much | Black | No Change |

*Calculated as metallic zinc stokes (100° C.), and the refractive index, $n_d^{20}$, was 1.5011. The cis-form content was 46% in the mixture. The traction coefficient was measured over a temperature range of from 30 to 140° C. The results are shown in FIG. 1.

The procedure of Example 5 was repeated except that 1-(1-decalyl)-2-cyclohexylethane prepared above was used in place of 1-decalyl-1-cyclohexylethane.

Input torque could not be transmitted at oil temperatures of 80° C. or more since the transmission was slipped.

We claim:

1. A traction drive fluid composition for use between at least two relatively rotatable elements in a torque transmitting relationship which comprises as the principal component at least one compound represented by the general formula (I):

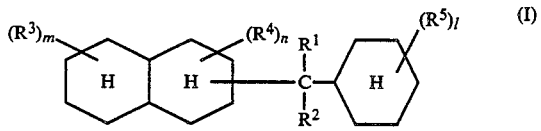

wherein $R^1$ to $R^5$ are each a hydrogen or an alkyl group containing from 1 to 4 carbon atoms, and l, m and n are each 1 to 3, said compound (I) comprising a mixture of 70% or less of the cis-form and 30% or more of the trans-form.

2. A traction drive fluid composition according to claim 1 in which the compound represented by the general formula (I) has the formula:

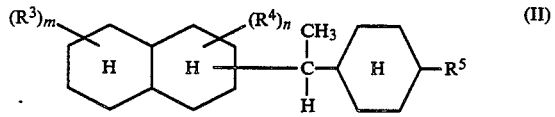

wherein $R^3$ and $R^4$ are each a hydrogen or a methyl group, $R^5$ is a hydrogen or a tert-butyl group, and m and n are each 1 or 2.

3. A traction drive fluid composition according to claim 2 in which the mixture comprises 30–60% of the cis-form and 70–40% of the trans-form.

4. A traction drive fluid composition according to claim 3 wherein the compound represented by the general formula (II) is 1-(2-decalyl)-1-cyclohexylethane.

5. A traction drive fluid composition according to claim 3 wherein the compound represented by the general formula (II) is 1-(1-decalyl)-1-cyclohexylethane.

6. A traction drive fluid composition according to claim 3 wherein the compound represented by the general formula (II) is 1-(2-decalyl)-1-(4-(tert-butyl)cyclohexyl)ethane.

7. A traction drive fluid composition according to claim 3 wherein the compound represented by the general formula (II) is 1-(1-decalyl)-1-(4-(tert-butyl)cyclohexyl)ethane.

8. A traction drive fluid composition according to claim 3 wherein the compound represented by the general formula (II) is 1-dimethyldecalyl-1-cyclohexylethane of the formula:

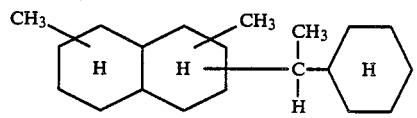

or

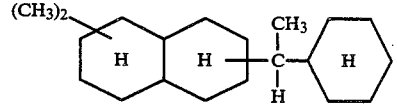

or

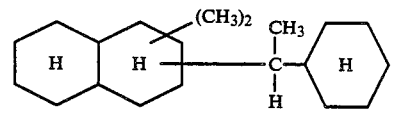

9. A traction drive fluid composition according to claim 3 wherein the compound represented by the general formula (II) is 1-methyldecalyl-1-cyclohexylethane of the formula:

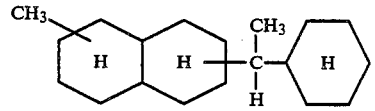

or

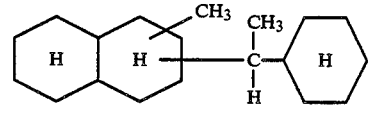

10. A process for improving the coefficient of traction between at least two relatively rotatable elements in a torque transmitting relationship and for maintaining said coefficient of traction substantially constant over a broad range of operating temperatures which comprises introducing between the tractive surfaces of said elements a traction drive fluid comprising at least one compound represented by the general formula (I):

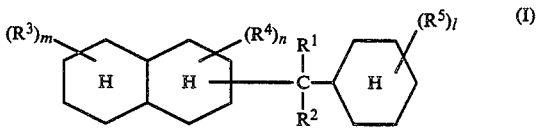

wherein $R^1$ to $R^5$ are each hydrogen or an alkyl group containing from 1 to 4 carbon atoms, and l, m and n are each 1 to 3, said compound (I) comprising a mixture of 70% or less of the cis-form and 30% or more of the trans-form.

11. A process according to claim 10 in which the compound represented by the general formula (II) has the formula:

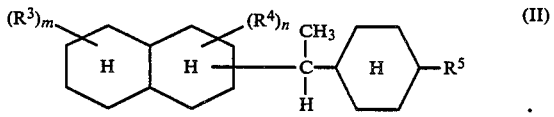

wherein $R^3$ and $R^4$ are each a hydrogen or a methyl group, $R^5$ is a hydrogen or a tert-butyl group, and m and n are each 1 or 2.

12. A process according to claim 11 in which the mixture comprises 30–60% of the cis-form and 70–40% of the trans-form.

13. A process according to claim 12 wherein the compound represented by the general formula (II) is 1-(2-decalyl)-1-cyclohexylethane.

14. A process according to claim 13 wherein the compound represented by the general formula (II) is 1-(1-decalyl)-1-cyclohexylethane.

15. A process according to claim 13 wherein the compound represented by the general formula (II) is 1-(2-decalyl)-1-(tert-butyl)cyclohexyl)ethane.

16. A process according to claim 13 wherein the compound represented by the general formula (II) is 1-(1-decalyl)-1-(4-(tert-butyl)cyclohexyl)ethane.

17. A process according to claim 13 wherein the compound represented by the general formula (II) is 1-dimethyl- decalyl-1-cyclohexylethane of the formula:

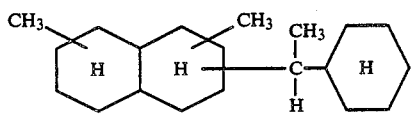

or

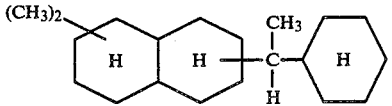

or

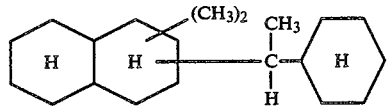

18. A traction drive fluid composition according to claim 13 wherein the compound represented by the general formula (II) is 1-methyldecalyl-1-cyclohexylethane of the formula:

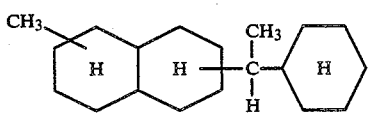

or

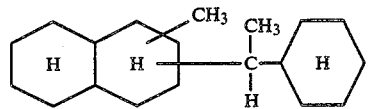

* * * * *